United States Patent
Jansen

(10) Patent No.: US 7,340,939 B2
(45) Date of Patent: Mar. 11, 2008

(54) EMISSIONS SAMPLING VALVE

(75) Inventor: Harvey B. Jansen, Mesa, AZ (US)

(73) Assignee: Jansen's Aircraft Systems Controls, Inc., Tempe, AZ (US)

(*) Notice: Subject to any disclaimer, the term of this patent is extended or adjusted under 35 U.S.C. 154(b) by 226 days.

(21) Appl. No.: 11/210,984

(22) Filed: Aug. 24, 2005

(65) Prior Publication Data

US 2006/0042701 A1 Mar. 2, 2006

Related U.S. Application Data

(60) Provisional application No. 60/604,270, filed on Aug. 25, 2004.

(51) Int. Cl.
*G01N 1/26* (2006.01)
*F16K 11/22* (2006.01)

(52) U.S. Cl. .................. 73/23.31; 73/863.33; 137/606; 251/63.4; 251/63.6

(58) Field of Classification Search ............. 137/606 I; 251/63.4 X, 63.6 X; 73/23.31 X, 863.33 X
See application file for complete search history.

(56) References Cited

U.S. PATENT DOCUMENTS

| | | | |
|---|---|---|---|
| 1,373,599 A * | 4/1921 | Clark ..................... | 137/596.18 |
| 1,714,626 A * | 5/1929 | Roberts ..................... | 105/48 |
| 3,572,366 A * | 3/1971 | Wiggins ..................... | 137/240 |
| 3,981,479 A * | 9/1976 | Foster et al. ................ | 251/63.6 |
| 4,231,392 A * | 11/1980 | Allibert ..................... | 137/454.2 |
| 4,414,858 A * | 11/1983 | Peterson et al. ......... | 73/863.33 |
| 4,455,837 A * | 6/1984 | Firey ........................... | 60/670 |
| 5,553,635 A * | 9/1996 | Gregoire ........................ | 137/1 |
| 6,050,081 A | 4/2000 | Jansen | |
| 6,094,968 A * | 8/2000 | Scheufler et al. ............ | 73/23.2 |
| 6,109,167 A * | 8/2000 | Vertanen ....................... | 92/253 |
| 6,931,831 B2 | 8/2005 | Jansen | |
| 2005/0056000 A1 | 3/2005 | Jansen et al. | |
| 2005/0097880 A1 | 5/2005 | Jansen | |

OTHER PUBLICATIONS

GE; 2004 Press Release: "GE Adds Predictive Emissions Monitoring Systems to Its Oil and Gas Offerings".
GE; GE Gas Turbine Performance Characteristics; dated Oct. 2000.

* cited by examiner

*Primary Examiner*—Stephen M. Hepperle
(74) *Attorney, Agent, or Firm*—Quarles & Brady LLP

(57) ABSTRACT

The invention provides a device for use in sampling the exhaust emissions from a turbine engine. The device has a valve array in a manifold housing coupling multiple turbine exhaust lines to an emissions analyzer, such as used in CEMS. Each valve can be actuated by pilot air pressure to open or close off flow of one or more of the exhaust lines. Exhaust from various zones of the turbine combustor section can be selectively sampled thereby allowing emissions measurements to be taken and used for compliance monitoring and performance and diagnostic analysis of turbine combustor operation.

18 Claims, 4 Drawing Sheets

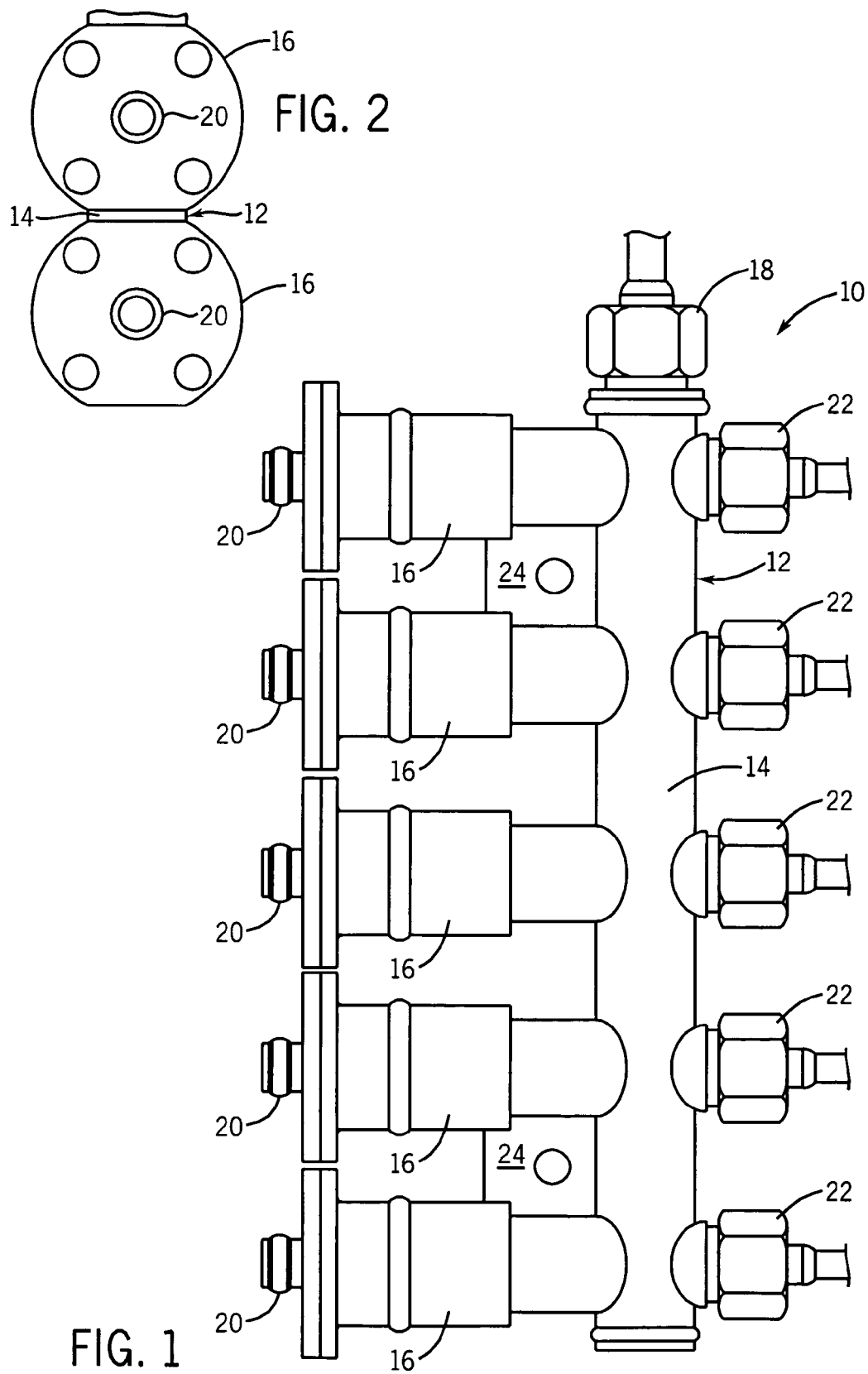

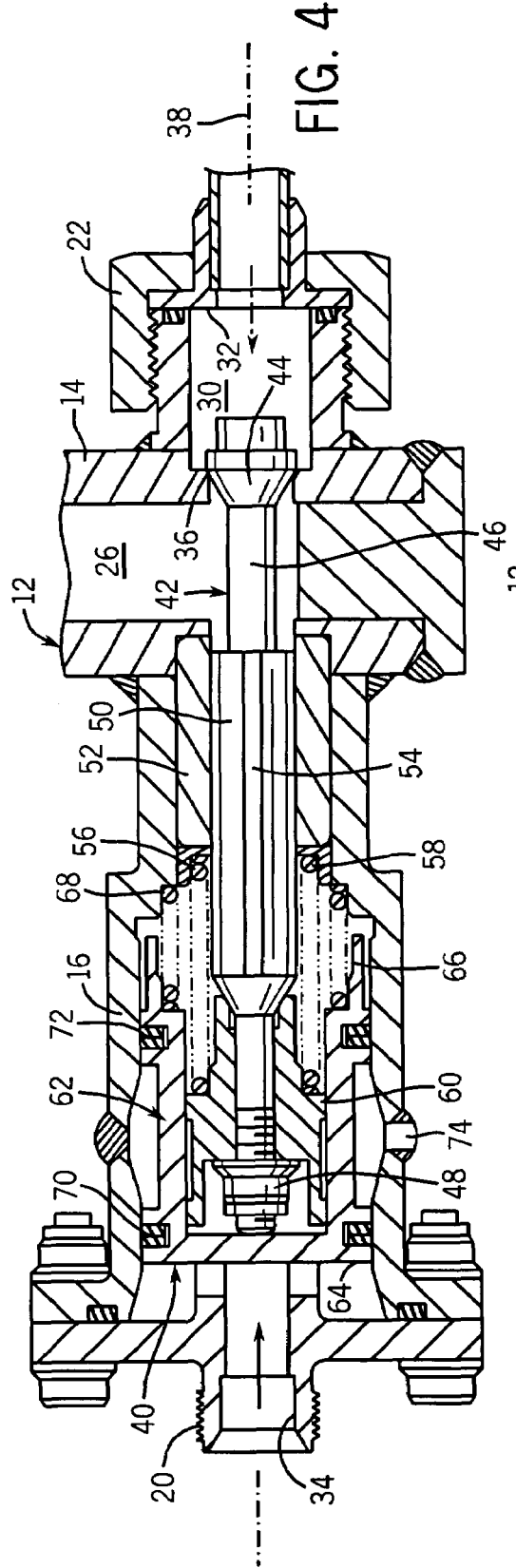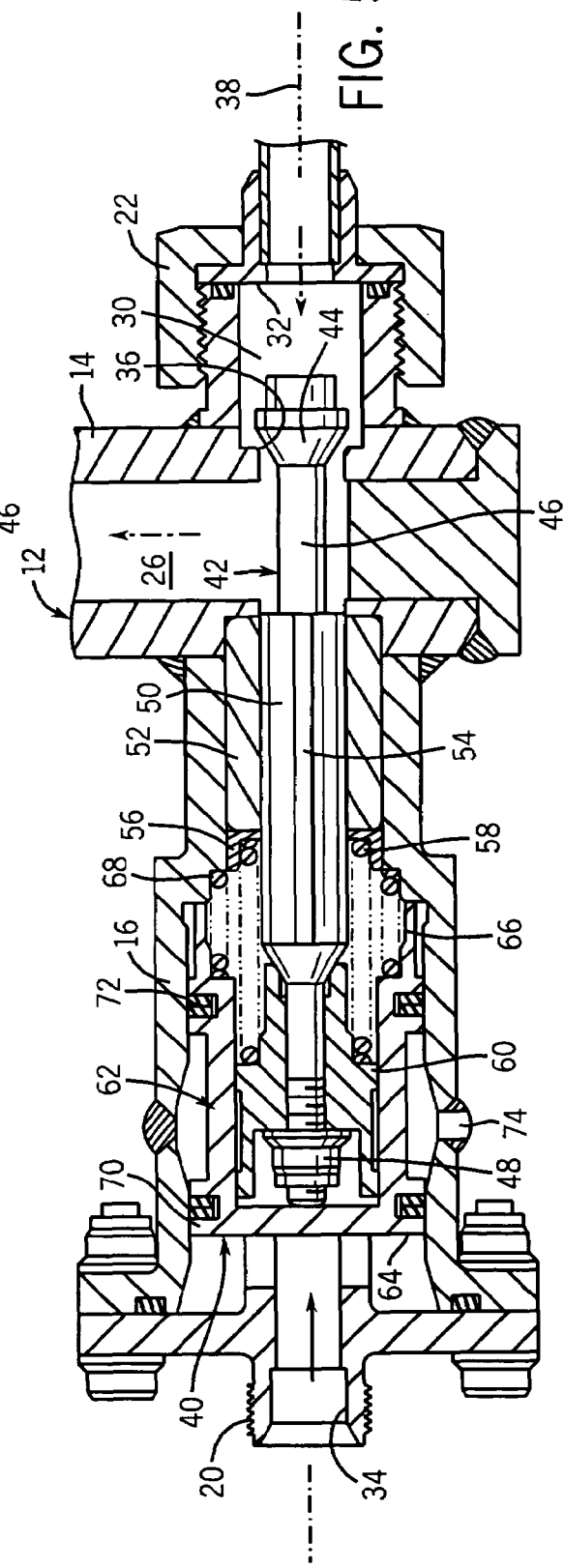

EMISSIONS SAMPLING VALVE

CROSS-REFERENCE TO RELATED APPLICATION

This application claims benefit to U.S. provisional application Ser. No. 60/604,270 filed Aug. 25, 2004.

STATEMENT OF FEDERALLY SPONSORED RESEARCH OR DEVELOPMENT

Not applicable.

BACKGROUND OF THE INVENTION

1. Technical Field

The present invention relates to gas turbine engines, and in particular, to devices for sampling turbine exhaust emissions.

2. Description of the Related Art

Gas turbine engines are commonly used in power generation and propulsion applications. Generally, gas turbine engines have a set of rotating turbine blades that compress air leading to one or more combustors into which fuel is injected and ignited. Fuel is delivered through metering orifices to burners in the combustors under pressure through a fuel line. Combustion of the fuel turns one or more sets of turbine blades, used for energy extraction or propulsion, and which can be used to drive the compressor blades.

Gas turbine engines are the main source of new power generation. To meet the rising energy demands, power plants operate the turbine engines essentially continuously. The byproducts of combusting hydrocarbon fuels, such as coal, include sulfur oxides (SOx), such as sulfur dioxide, carbon oxides (COx), such as carbon monoxide and carbon dioxide, and nitrogen oxides (NOx), such as nitric oxide. These byproducts, particularly NOx, have been thought to play a role in a wide variety of health and environmental issues including smog, acid rain and global warming.

These health and environmental concerns have prompted the Environmental Protection Agency and local legislators to promulgate emission standards for power plants. To meet the emission standards, low NOx combustors were devised which provide staged combustion to limit the amount of air in the initial stages of combustion when fuel bound nitrogen is released and also to reduce the flame temperature during some phases of combustion. Many power plants have also converted to using gas turbines that burn natural gas for sustained operation after being ignited by a fossil fuel, such as liquid diesel fuel. Natural gas burns cleaner than fossil fuels, with significantly lower NOx and COx emissions.

However, as emission standards become increasingly stringent with regard to SOx, COx and NOx, as well as other post-combustion components, such as mercury, control of emissions remains a significant issue. Not only are power plants being held to strict emissions standards, it is becoming increasingly common for the emissions to be monitored continuously, using either a Predictive Emissions Monitoring System (PEMS), which uses an algorithm to model various exhaust emissions components based on turbine operating parameters such as fuel consumption and certain ambient conditions, or a Continuous Emissions Monitoring System (CEMS). A CEMS uses actual samples of turbine exhaust to analyze and record pertinent emission contents. CEMS analyzers are commercially available from K2BW Environmental Equipment Services, Company of Willow Grove, Pa.

For the CEMS, an electronic analyzer device is coupled to the gas turbine exhaust. One or more valves may be placed in-line with turbine exhaust line(s) to shut-off flow to the analyzer should monitoring need to be discontinued, for example, during engine shut down or to service the analyzer. These shut-off valves are typically manually controlled, however, it would be feasible to incorporate an electronically controlled valve to automate the exhaust shut-off to the analyzer. However, the exhaust environment of conventional industrial gas turbines is rather extreme, typically in the range of 1,200-1,300° F. and laden with particulate matter, such that conventional valving is typically unsuitable.

Moreover, the conventional CEMS is designed to provide emissions readings for the pertinent constituent parts of the exhaust for the turbine overall. However, many gas turbines have multiple discrete combustion zones. For example, the large industrial gas turbines used in modern power plants today typically have 14-16 annular combustion zones or combustor cans, each having a dedicated burner nozzle and fuel supply line. The gas turbine may operate with fuel burning in all or only a portion of the combustion zones depending on the power demand and other factors. Thus, it may be desirable to close off one or more exhaust outlet lines corresponding to inactive combustion zones of the turbine, while leaving the exhaust lines corresponding to the fired zones open. It may also be desired to selectively analyze exhaust from one or a select number of operating combustion zones. Further, it would be desirable to use the data from the emissions analysis as feedback for the turbine combustion performance, at one or more of the combustion zones, for example to pinpoint a high NOx emission combustor or a problem with one or more of the burner nozzles.

Since conventional systems do not provide suitable valving to achieve the desired control of turbine exhaust sampling, an improved emissions sampling valve is needed.

SUMMARY OF THE INVENTION

The present invention is a device for collecting gas turbine exhaust for analysis of its emissions. The emissions sample can then be used to identify and measure constituent emission components as well as identify areas of interest to turbine operation in the combustor. The device has one or more valves operated by pilot air pressure to control flow from one or more inlets to an outlet that can be coupled to an electronic analyzer. The number of valves and inlets can be selected according to the number of discreet combustion zones or combustor cans present in the turbine. The valve(s) can be controlled individually or collectively, and preferably, each valve is normally positioned to close off exhaust flow and is opened by pilot air pressure.

In one aspect the invention provides a sampling valve having a housing defining a sample passageway leading to a sample outlet and defining a valve passageway that intersects the sample passageway and extends along a valve axis between a pilot air inlet and a sample inlet. A valve is disposed within the valve passageway that has a valve head which is matable with a valve seat located between the sample inlet and the sample passageway. The valve is moveable along the valve axis by application of pilot air pressure through the pilot air inlet. In a closed position, the valve head is seated against the valve seat to close off the sample passageway from the sample inlet. In an open position, the valve head is unseated from the valve seat so that the sample passageway is open to the sample inlet.

In another aspect the invention is an emissions sampling valve having a valve array in a manifold housing for coupling multiple turbine exhaust lines to an emissions analyzer, such as used in CEMS. As one example, the emissions sampling valve can have one valve and sample inlet dedicated to each combustion zone or bank of combustor cans of the gas turbine engine. Regardless of the precise number of valves, the emissions sampling valve allows exhaust from various zones of the turbine combustor section to be selectively sampled, thereby allowing emissions measurements to be used both for compliance monitoring as well as performance and diagnostic analysis of turbine combustor operation.

Each valve is disposed in its own valve passageway, which are preferably arranged in parallel and intersect a common sample passageway upstream from the sample outlet and between the corresponding pilot air pressure inlet and the corresponding sample inlet. Each valve seat is located in its valve passageway upstream from the sample passageway so that when the mating valve head is seated therein it will obstruct flow from the corresponding inlet.

The pilot air pressure can be instrument air or compressor discharge air and can be used to either actuate the valves or to hold them in a normally open or closed state. In either case, a biasing member would be used to return each valve to its opposite position in the absence of the pilot air pressure. Preferably, each valve is held biased in the closed position and is actuated open by the pilot air pressure.

The valves can be poppet type valves driven by the force of pilot air pressure acting against the enlarged heads of drive pistons. The drive pistons and the valves can be biased by return springs against the driving force so that the valves return to their original closed position in the absence of pilot air pressure. A retainer can be mounted to each valve that can slide within an inner bore of the piston. The valve return spring can then bear against the retainer and a spacer cup. Piston rings seal the valve passageways to isolate the pilot air from the sample flow. An interstitial vent can be provided to further ensure that the pilot air does not contaminate the sample flow.

The invention thus provides an emissions sampling device with a manifold mounted valve array. The sampling valve provides for collection of emissions samples that are indicative of the aggregate exhaust from all or a set of combustion zones of the turbine or from a selected combustion zone, thereby allowing an individual high emissions combustor to be detected, for example. The valves are constructed and their materials are selected to allow for extended operation in a contaminated and elevated temperature environment with high oxidation resistance and long life. The pilot air used to control valve positioning can be separate instrument air or can utilize turbine compressor discharge air such that a separate air stream need not be provided. In either case, the pilot air is segregated from the sample flow so as not to introduce contaminants into the sample or into the valve passageways.

These and still other advantages of the invention will be apparent from the detailed description and drawings. What follows is a preferred embodiment of the present invention. To assess the full scope of the invention the claims should be looked to, as the preferred embodiment is not intended as the only embodiment within the scope of the invention.

BRIEF DESCRIPTION OF THE DRAWINGS

FIG. 1 is a top plan view of a pilot air operated emissions sampling valve of the present invention;

FIG. 2 is a partial end elevational view thereof;

FIG. 4 is a cross-sectional view of the sectioned valve arrangement of FIG. 3 showing the valve in a closed position;

FIG. 5 is a cross-sectional view similar to FIG. 4 albeit showing the valve in an open position.

DETAILED DESCRIPTION OF THE PREFERRED EMBODIMENT

Figure 3:
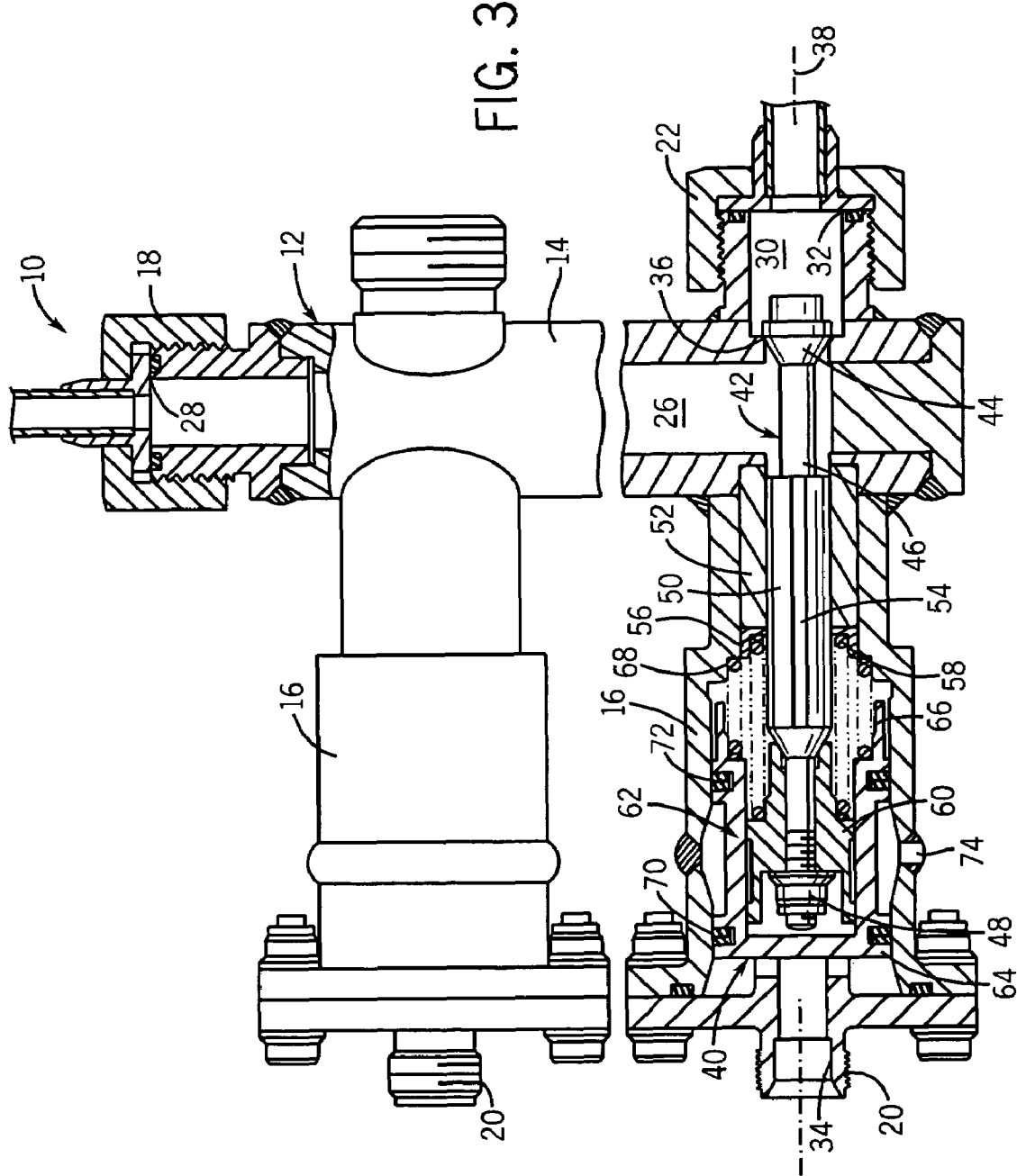
FIG. 3 is partial top plan view thereof showing one valve arrangement in cross-section.

Referring to FIGS. 1 and 2 of the drawings, an emissions sampling valve 10 has a manifold 12 defining a sample section 14 and five identical valve sections 16. While the illustrated embodiment has five valve sections, any number could have been provided, for example two, three or a number corresponding to the number of combustion zones of the turbine combustor section or in a quadrant or other portion thereof. The sample housing 14 is capped at one end and has an outlet fitting 18 at the other end. The valve sections 16 each have a pilot air fitting 20 at one end and an exhaust sample inlet fitting 22 at the other end. All of the fittings are preferably of standard size and type as used in the industry, such as standard sized compression fittings, and have metal crush gaskets at the flanges. Mounting brackets 24 are provided to secure the sampling valve 10 to or near the turbine.

With reference to FIGS. 3-5, the manifold 12 interior defines a sample passageway 26 at the sample section 14 in communication with an outlet 28. Each valve section 16 defines a valve passageway 30 (one shown), in communication with an exhaust sample inlet 32 (one shown) and a pilot air inlet 34 (one shown), that intersects the sample passageway 26. Circular transverse openings in the sample section 14 define conical valve seats 36 (one shown), each of which is concentric with a valve axis 38 extending lengthwise through the center of each valve passageway 30.

As with the exterior, the internal components of each valve section 16 are identical, and as such, only one valve assembly 40 will be described in detail herein. The valve assembly 40 includes an elongated poppet valve 42 disposed along the valve axis 38. The poppet valve 42 defines a partial conical valve head 44 at one end that mates with the corresponding valve seat 36 (as shown in FIG. 4). The poppet valve 42 has a long stem 46 that is threaded at the end opposite the valve head 44 to receive nut 48. An enlarged barrel section 50 extends lengthwise near the middle of the poppet valve 42. The barrel 50 of the valve slides within a bore of a guide bushing 52. The barrel 50 has three lengthwise flutes 54 (one shown) that can accommodate small particles that could otherwise cause the valve to bind. Upstream from the guide bushing 52 is a ring spacer 56 that captures a valve return spring 58, which presses against a retainer 60 secured to the poppet valve 42 by the nut 48. The retainer 60 and spring 58 arrangement thus holds the guide bushing 52 in place, which is beneficial because the spring can accommodate thermal expansion and contraction without generating excessive structural forces. The retainer 60 slides within an inner bore of a drive piston 62. The drive piston 62 has an enlarged circular head 64 at one end and an annular tail 66 at the opposite end in which fits a piston return spring 68 extending between internal shoulders of the valve section 16 and the piston 62.

The piston 62 has two pairs of high temperature piston rings 70 and 72 spaced apart near the head 64 and the tail 66 that create a sliding seal against the inner bore of the valve section 16 defining the valve passageway 30. Between the pairs of piston rings 70 and 72, an annular channel is defined between the piston 62 and the valve section 16. A small hole 74 provides an interstitial vent between the pilot air and the sample flow so that any leakage across the seals 70 and 72 can be discharged from the unit rather than contaminate the sample flow stream. Thus, the piston rings 70 at the head 64 primarily seal the pilot air from ambient and the piston rings 72 near the tail 66 primarily seal the sample passageway 26 from ambient.

Due to the extended use of the emissions sampling valve 10 and the extreme temperatures present, which typically range from 1,200-1,300° F., and the propensity for oxidation to occur at the turbine exhaust, most of the components of the sampling valve are made of a suitable metal, preferably a suitable grade of stainless steel. The guide bushing 52, however, is preferably a high-temperature non-metallic material, such as a carbon or ceramic, to prevent galling of the poppet valve 42.

FIGS. 4 and 5 illustrate the two extreme positions of the valve assembly 40. Specifically, the valve assembly 40 is shown in the closed position in FIG. 4 in which the valve head 44 is seated in the valve seat 36, in metal-to-metal surface contact, so that turbine exhaust through the corresponding exhaust inlet 32 is isolated from the sample passageway 26. The valve assembly 40 is shown in the open position in FIG. 5 in which the valve head 44 is unseated from the valve seat 36 so that turbine exhaust can pass from the corresponding exhaust inlet 32 to the sample passageway 26.

In the preferred embodiment disclosed herein, the valve assembly 40 is normally in the closed position of FIG. 4. It is biased in this position by the return springs 58 and 68, which provide a relatively high pre-load on the poppet valve 42, for example 25 pounds or greater, so that high sealing forces are provided at the valve seat to ensure a reliable seal when not sampling as well as an adequate return force for resetting the valve assembly 40. The valve assembly 40 is actuated to the open position of FIG. 5 by pressure from pilot air passing through the corresponding pilot air inlet 34 and acting against the head 64 of the drive piston 62. The pilot air pressure forces the piston 62 to translate along the valve axis 38 (from left to right in the figures) against the bias of the piston return spring 68. As the piston 62 moves an inside surface of the head 64 abuts the end of the valve stem 46 and drives the poppet valve 42 against the bias of the valve return spring 58. The pilot air pressure thus works against the cumulative forces of the springs 58 and 68 to drive the piston 62 and the poppet valve 42 in the direction to unseat the valve head 44 from the valve seat 36. In the open position of FIG. 5, the valve head 44 is unseated and the tail 66 of the piston 62 bottoms against an internal shoulder of the valve section 16 to stop further movement of the piston 62 and poppet valve 42 and prevent excessive loading on the poppet valve 42 during acquisition of a sample. When pilot air pressure is sufficiently decreased or terminated, the return springs 58 and 68 will reset the valve assembly 40 to its normally closed position of FIG. 4.

Figure 6:
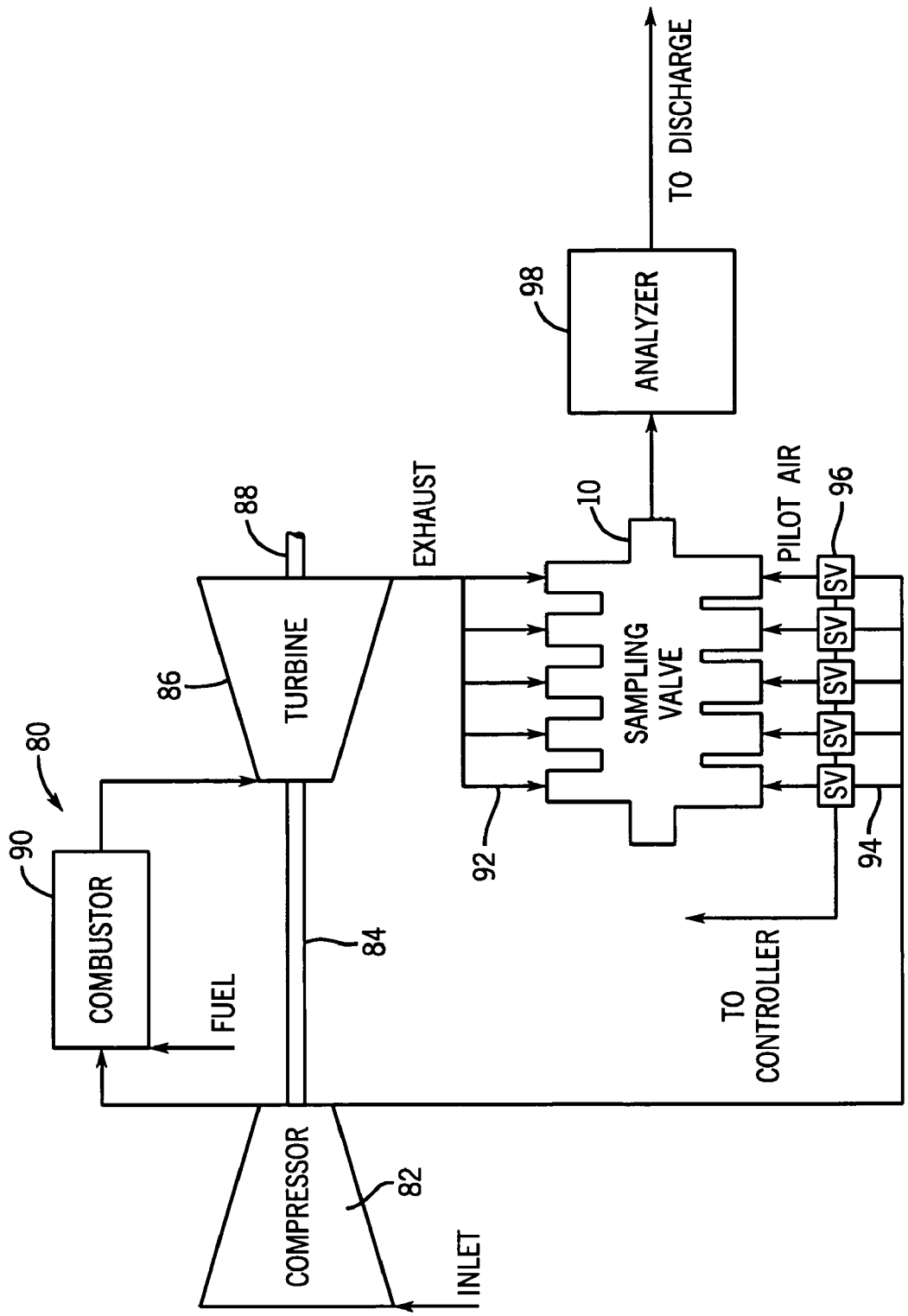
FIG. 6 is a schematic diagram of the emissions sampling valve in a simplified industrial gas turbine system.

FIG. 6 illustrates schematically a simplified industrial gas turbine 80 incorporating the emissions sampling valve 10 of the present invention with a Continuous Emissions Monitoring System (CEMS). As is conventional, the gas turbine system 80 has a compressor section 82 that is mechanically coupled by a shaft 84 to a turbine section 86, for example including a primary set of turbine blades that are air coupled to a power turbine which drives an output shaft 88 for power generation. Between the compressor 82 and turbine 86 sections is a combustor section 90 that can include one or more discrete combustion chambers, typically in the form or annularly disposed combustion zones or cans arranged about the shaft 84 and having dedicated burner nozzles (not shown). Conventional industrial gas turbines used for power generation typically have 14-16 such discrete combustion zones. As is conventional, inlet air is pressurized and accelerated by the compressor 82 and is fed into the combustor section 90 where fuel is introduced and ignited. The pressurized air is thus heated and allowed to expand as it passes through the turbine section 86, thereby increasing its volume significantly and producing energy to drive the output shaft 88, and also the compressor blades if desired.

The spent air from the turbine section 86 is passed through an exhaust manifold or one or more discrete outlets through lines 92 to the exhaust inlet fittings (22 in FIG. 2) of the emissions sampling valve 10. To operate the emissions sampling valve 10, some of the compressor discharge air is directed through lines 94. Computer controlled solenoid valves 96 are used to control flow of the compressor discharge pilot air from the lines 94 into the pilot air inlets (36 in FIG. 3). The solenoid valves 96, and thereby the valve assemblies (40 in FIG. 3) can be controlled collectively or individually so that one or a selected set of the valves are opened. In any event, when one or more of the valves are opened (as shown in FIG. 5) the turbine exhaust flow is passed through the sample passageway (26 in FIG. 3) and onto the GEMS analyzer 98, where various emissions components, such as SOx, GOx and NOx, are detected, measured and recorded. After passing through the analyzer the exhaust can be fed to an air discharge system of the power plant or recirculated through the gas turbine system, depending on the type of turbine system utilized. Similarly, bypass valve(s) and line(s) (not shown) can be provided at the turbine exhaust to redirect exhaust flow to return or discharge when one or more of the valves of the emissions sampling valve are closed.

It has been found that the air flow from the combustor section tends to remain striated as it passes through the turbine section such that exhaust at particular locations of the turbine section can correspond to particular combustion zones in the combustor section. Thus, properly controlled sampling of the turbine exhaust can be used not only to provide data regarding emissions components generally, but also feedback on the state of particular combustion zones.

The emissions sampling valve 10 of the present invention can be used, for example, to diagnose and pin-point the source of operational problems with the turbine. For example, low turbine efficiency or low power output could be caused by one of the combustion zones not firing or not firing at full capacity. This could result from a plugged burner nozzle or fuel injector in one of the combustion zones. In conventional turbine systems, this problem would be diagnosed by looking at the readings of various sensors placed at each combustion zone. Since modern industrial gas turbines have several (14 or so) combustion zones this requires a significant amount of additional equipment and assembly, including sensors, wiring and electronic measurement devices. With the present invention, the emissions sampling valve would simply be controlled to open one valve assembly at a time so that a sample of emissions from each combustion zone can be collected individually. Or, sets of valve assemblies can be opened to collect samples first collectively from a bank of combustor cans, then once a particular bank of combustor cans is identified as problematic, each of the combustor cans in that bank can be individually sampled. Thus, for example, one valve assembly can be opened to sample turbine exhaust corresponding to combustor can No. 3. Analysis of the emissions could, for example, reveal extremely low or no emissions readings corresponding to can No. 3, which would indicate that can No. 3 had a plugged fuel injector. The same type of procedure could be used to diagnose and pin-point the source of other combustion problems including a plugged burner nozzle as mentioned above, which could be identified by an unusually high emissions reading.

Thus, the present invention provides a sampling valve for coupling turbine exhaust to a CEMS analyzer for acquisition of turbine exhaust samples for measuring overall turbine emissions. Multiple turbine locations can be coupled to the sampling valve and exhaust from various parts of the combustor section can be selectively sampled. The selective sampling provided by the sampling valve allows technicians to interpret emissions readings as feedback on the state of specific combustion zones of the combustor section, thereby helping to detect the locus of high emissions, turbine inefficiency or the like.

It should be appreciated that merely a preferred embodiment of the invention has been described above. However, many modifications and variations to the preferred embodiment will be apparent to those skilled in the art, which will be within the spirit and scope of the invention. Therefore, the invention should not be limited to the described embodiment. To ascertain the full scope of the invention, the following claims should be referenced.

I claim:

1. A system for sampling exhaust emissions from a gas turbine having multiple combustion zones, comprising:
   an electronic controller;
   a sampling manifold defining a sample passageway between a sample outlet and a plurality of inlets and defining a plurality of valve passageways arranged for communication with the sample passageway, each of the plurality of valve passageways having a sampling valve movable by pilot air pressure between a closed position in which the associated inlet is closed off from the sample passageway and an open position in which the associated inlet is open to the sample passageway; and
   a plurality of control valves each being associated with one of the sampling valves and being operated by the controller to control flow of pilot air to the associated sampling valve;
   wherein the controller operates one or more of the control valves to selectively sample emissions from one or more selected combustion zones of the turbine.

2. The system of claim 1, further including an analyzer receiving output from the sampling manifold and analyzing emission content.

3. The system of claim 1, wherein at least one of the sampling valves is associated with one of the combustion zones of the turbine.

4. The system of claim 1, wherein the sampling manifold has at least three sampling valves.

5. The system of claim 1, wherein the sampling valves extend along essentially parallel axes that are essentially perpendicular to the sample passageway.

6. The system of claim 1, wherein the pilot air is segregated from the sample passageway.

7. The system of claim 1, wherein each sampling valve is biased in the closed position and is actuated to open by the pilot air.

8. The system of claim 1, wherein the sampling valves are poppet valves.

9. The system of claim 1, wherein each sampling valve includes a piston having an enlarged piston head against which the pilot air acts to drive the associated sampling valve.

10. The system of claim 9, wherein the piston includes a piston seal on each side of an annular interior chamber in which an associated sampling valve is disposed.

11. The system of claim 10, wherein the sampling manifold defines an interstitial vent in communication with the interior chamber of each sampling valve and being essentially separated from the pilot air by the piston seal.

12. The system of claim 9, wherein each sampling valve further includes a return spring bearing against the associated piston to bias the piston against the pilot air pressure.

13. The system of claim 12, wherein each sampling valve further includes a second return spring biasing the associated sampling valve to the closed position.

14. The system of claim 13, wherein each sampling valve further includes a retainer mounted to the associated sampling valve and slidable with respect to its piston.

15. The system of claim 14, wherein the second return spring bears against the associated retainer.

16. The system of claim 15, wherein each sampling valve further includes a spacer cup and wherein the associated second return spring is captured between the associated retainer and spacer cup.

17. The system of claim 16, wherein each piston as an inner bore and wherein each retainer is disposed within the inner bore of the associated piston.

18. The system of claim 17, wherein each sampling valve further includes a guide bushing having an inner bore receiving an enlarged diameter barrel section of the associated sampling valve.

* * * * *

UNITED STATES PATENT AND TRADEMARK OFFICE
CERTIFICATE OF CORRECTION

PATENT NO. : 7,340,939 B2
APPLICATION NO. : 11/210984
DATED : March 11, 2008
INVENTOR(S) : Harvey B. Jansen It is certified that error appears in the above-identified patent and that said Letters Patent is hereby corrected as shown below:

Col. 6, Line 29:
"GEMS" should be --CEMS--

Col. 6, Line 30:
"GOx" should be --COx--

Signed and Sealed this

Twelfth Day of August, 2008

JON W. DUDAS
*Director of the United States Patent and Trademark Office*